(12) United States Patent
Chang et al.

(10) Patent No.: US 8,669,358 B2
(45) Date of Patent: Mar. 11, 2014

(54) VANADIUM PHTHALOCYANINE COMPOUNDS AND NEAR-INFRARED ABSORPTION FILTER USING THE SAME

(75) Inventors: Yu-Mi Chang, Gyeonggi-do (KR); Ju-Sik Kang, Gyeonggi-do (KR); Jeong-Ho Park, Gyeonggi-do (KR)

(73) Assignee: SK Chemicals Co., Ltd., Suwon-Si (KR)

( * ) Notice: Subject to any disclaimer, the term of this patent is extended or adjusted under 35 U.S.C. 154(b) by 18 days.

(21) Appl. No.: 13/142,722

(22) PCT Filed: Nov. 5, 2009

(86) PCT No.: PCT/KR2009/006494
§ 371 (c)(1),
(2), (4) Date: Jun. 29, 2011

(87) PCT Pub. No.: WO2010/076968
PCT Pub. Date: Jul. 8, 2010

(65) Prior Publication Data
US 2011/0275847 A1    Nov. 10, 2011

(30) Foreign Application Priority Data
Dec. 31, 2008    (KR) .................. 10-2008-0138356

(51) Int. Cl.
*C09B 47/04*    (2006.01)
*C07F 9/00*    (2006.01)

(52) U.S. Cl.
USPC ............................................ 540/140; 556/35

(58) Field of Classification Search
USPC ............................................ 556/35; 540/140
See application file for complete search history.

(56) References Cited

U.S. PATENT DOCUMENTS

| | | | | |
|---|---|---|---|---|
| 5,024,926 A | * | 6/1991 | Itoh et al. | 430/495.1 |
| 5,124,067 A | * | 6/1992 | Itoh et al. | 252/299.2 |
| 6,323,340 B1 | * | 11/2001 | Masuda et al. | 540/128 |
| 6,824,712 B1 | * | 11/2004 | Yang et al. | 252/582 |
| 7,314,511 B2 | * | 1/2008 | Campbell et al. | 106/31.49 |
| 2003/0234995 A1 | | 12/2003 | Masuda et al. | |
| 2004/0023146 A1 | | 2/2004 | Maemoto et al. | |
| 2005/0203293 A1 | | 9/2005 | Hirota et al. | |

FOREIGN PATENT DOCUMENTS

| | | |
|---|---|---|
| JP | 2005-220060 A | 8/2005 |
| JP | 2007-169343 A | 7/2007 |
| KR | 2003-0095052 A | 12/2003 |
| KR | 10-2004-0049280 A | 6/2004 |
| KR | 10-0565475 B1 | 3/2006 |
| KR | 10-2006-0043681 A | 5/2006 |
| KR | 10-0722795 B1 | 5/2007 |

* cited by examiner

*Primary Examiner* — Johann R. Richter
(74) *Attorney, Agent, or Firm* — Birch, Stewart, Kolasch & Birch, LLP

(57) ABSTRACT

A vanadium phthalocyanine compound with low absorptivity in the visible light region and high absorptivity in the near-infrared light region, and represented by the following Formula:

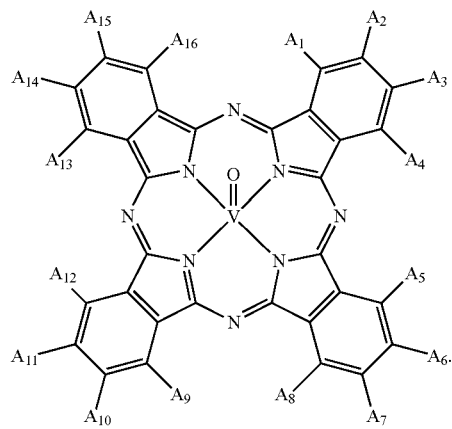

4 Claims, 2 Drawing Sheets

VANADIUM PHTHALOCYANINE COMPOUNDS AND NEAR-INFRARED ABSORPTION FILTER USING THE SAME

TECHNICAL FIELD

This invention relates to a vanadium phthalocyanine compound and a near-infrared absorption filter using the same, and more particularly to a novel vanadium phthalocyanine compound having low absorptivity in the visible wavelength region and high absorptivity in the near-infrared wavelength region, and a near-infrared absorption filter using the same.

BACKGROUND ART

Phthalocyanine compounds which were originally developed as pigments are thermally and chemically stable. Besides, their solubility and absorption property can be changed with their structural characteristics by introducing various substituents at the outer structure of them. Therefore, phthalocyanine compounds are being widely used in various uses which require thermal and chemical stability, especially, in various electronics industry fields, according to the recent explosive growth of electronics industry, for example, in uses such as pigments applied in organic photo conductor for laser print, near-infrared absorption materials for PDP (plasma display), sensitizers for solar cell, and so on.

Especially, according to the recent rapid expansion of the display industry, the usage of near-infrared absorption filter for PDP is sharply increasing, thus, the demand of near-infrared absorption materials is increasing. The near-infrared absorption filter for PDP is used to block the light in the near-infrared light region which is one of various light sources generated from PDP and may cause malfunction of the home remote control. A near-infrared absorption pigment which is used in the near-infrared absorption filter must increase transmittance of the visible light generated from light source and improve color gamut (color reproductivity) of display devices by having superior light absorption property in the region of 800 to 1100 nm and low light absorption property in the visible light region. Also, the near-infrared absorption pigment must have solubility, weather resistance, durability, and so on, for the convenience of process. As the near-infrared absorption pigment, representatively, the above stated cyanine based compounds, nickel-dithionyl based compounds, diimonium based compounds and so on, are known. However, the cyanine based compounds are difficult to be applied actually because of lack of heat resistance, and the diimonium based compounds are not suitable for the near-infrared absorption filter method of coating type which is being used recently in display industry, because of lack of durability to the environment such as moisture. Also, the nickel-dithionyl based compounds are limited in application, because of low solubility, even though they have an advantage of low light absorption property in the visible light region.

On the other hand, the phthalocyanine compounds are superior to other compounds in durability and weather resistance, and can solve the problem of solubility by controlling the substituent of the outer of structure, and can increase light absorptivity rather freely in the most near-infrared light region of 800 to 1100 nm, so that they are known to be suitable for the coating type near-infrared absorption filter method for PDP. However, conventional phthalocyanine compounds for the absorption of near-infrared light have superior photosensitive characteristic mainly in the region of 900 to 1000 nm, but have a disadvantage in that light absorptivity in the visible light region is a little higher than nickel-dithionyl based compounds and so on and color gamut is decreased, Also, the light absorptivity of conventional phthalocyanine compounds is not fully enough in the region of 880 to 920 nm which occupies the largest portion in the near-infrared light generated from the light source for PDP. Therefore, various studies for increasing the light absorptivity in the region of the above stated main wavelength by changing the central metal of phthalocyanine compound or the substituents of the outer of compound structure, have been done. However, in the case that a substituent such as a phenol, a thiophenol, first amine, and so on is introduced, the light absorptivity in the visible light region is increased too and color gamut is decreased, then applications are limited.

DISCLOSURE

Technical Problem

Therefore, it is an object of the present invention to provide a vanadium phthalocyanine compound with high absorptivity in the near-infrared light region, especially the region of 880 to 920 nm, and low absorptivity in the visible light region, which can provide superior color gamut (color reproductivity).

It is another object of the present invention to provide a near-infrared absorption filter using the vanadium phthalocyanine compound which can have superior near-infrared absorption property and color gamut.

Technical Solution

In order to achieve these objects, the present invention provides a near-infrared absorption vanadium phthalocyanine compound represented by following Formula 1.

[Formula 1]

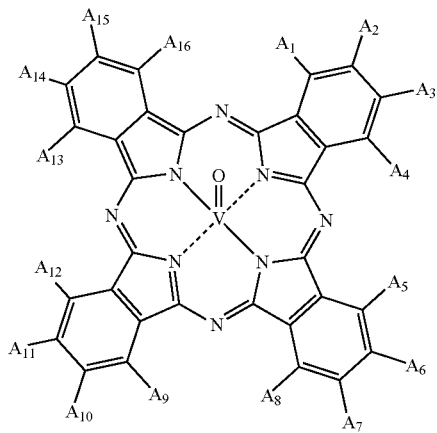

In Formula 1, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least one thereof is $NR_3R_4$, and at least four thereof are $OR_1$; $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms.

The present invention also provides a near-infrared absorption filter which comprises the near-infrared absorption vanadium phthalocyanine compound.

Advantageous Effects

A vanadium phthalocyanine compound according to the present invention has maximum absorptivity in the wavelength of 850 to 950 nm, particularly 880 to 930 nm. The transmittance of the compound in the visible light region, for example, at 450 nm is excellent (more than 90%) when the transmittance at the wavelength of the maximum absorptivity is 10%.

MODE FOR INVENTION

Figure 1:
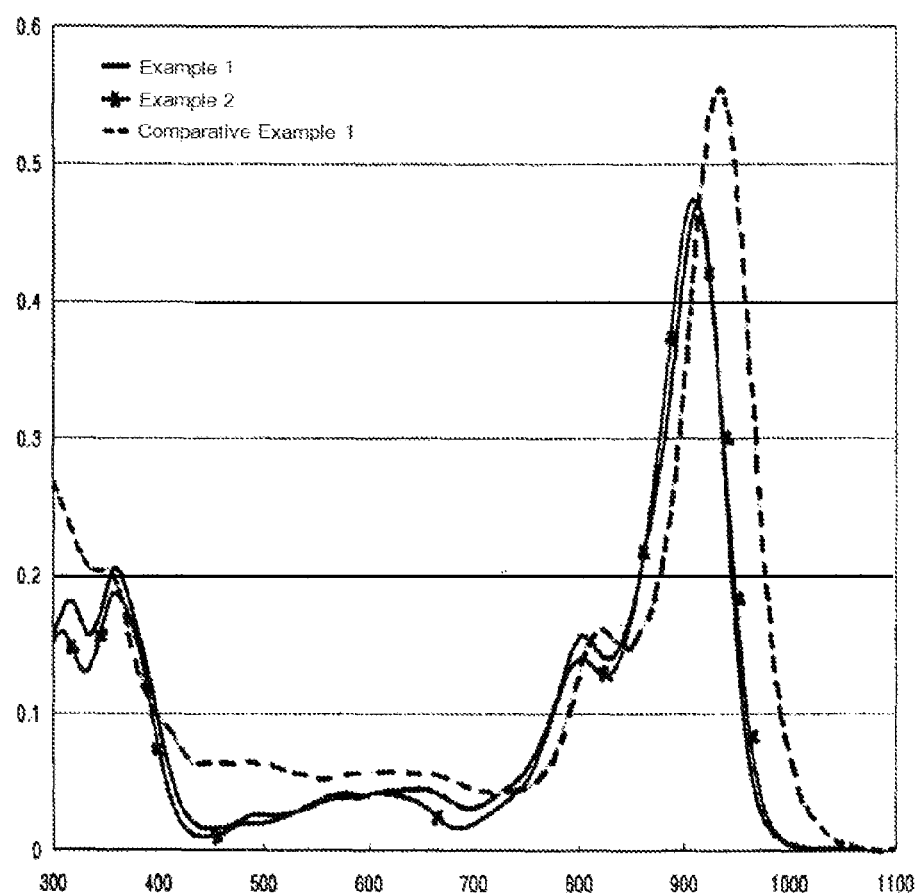
FIG. 1 shows UV/VIS absorption spectra of vanadium phthalocyanine compounds prepared in Example 1 and 2 and Comparative Example 1.

A more complete appreciation of the invention, and many of the attendant advantages thereof, will be better appreciated by reference to the following detailed description.

A vanadium phthalocyanine compound in the present invention is a near-infrared absorption compound whose light absorptivity in the near-infrared light region is superior and light absorptivity in the visible light region is low, and is represented by following Formula 1.

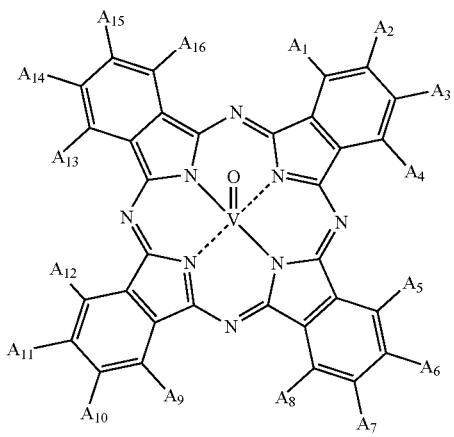

[Formula 1]

In Formula 1, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least one thereof is $NR_3R_4$, and at least four thereof are $OR_1$; $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms. $R_3$ and $R_4$ can be connected to each other to form a cyclic structure.

The preferable example of the halogen atom is a fluorine atom, and preferably, at least one of the $A_1$ to $A_{16}$ is a fluorine atom or $NR_3R_4$. Also, it is preferable that $R_3$ and $R_4$ are connected to each other to form a cyclic structure, and in this case, $NR_3R_4$ can form a heterocyclic compound of 4 to 20 carbon atoms, preferably, 4 to 8 carbon atoms such as pyrrolidine, piperidine, and so on. Also, if necessary, $R_1$, $R_2$, $R_3$ and $R_4$ can have a substituent such as an alkyl group of 1 to 10 carbon atoms, a halogen group, and so on.

The phthalocyanine compound of Formula 1, can block the light of wavelength of 850 to 950 nm by introducing a vanadium as a central metal in the phthalocyanine structure, and can effectively block the light of the near-infrared light region, especially the region of 880 to 920 nm and have high transmission ability of visible light by introducing a secondary amine as a substituent. Therefore, the phthalocyanine compound has superior durability and weather resistance, and a characteristics that light absorption ability in the near-infrared light region of 880 to 930 nm, preferably 880 to 920 nm wavelength is superior and light absorption in the visible light region is very low. Particularly, the phthalocyanine compound has 90% or more transmittance (T %) in the visible light region (wavelength of about 450 nm) when its transmittance at the maximum absorption wavelength in the near-infrared light region (wavelength of 880 to 920 nm) is 10%.

As well known by various papers or patents, the phthalocyanine compound of Formula 1 can be synthesized by reaction of a substituted dicyanobenzene or a substituted diimino isoindoline with suitable catalyst at high temperature. For example, as disclosed in papers and patents such as Inorg. Chem. 1995, 34, 1636-1637, Japanese patent publication No. 1997-316049, and so on, the phthalocyanine compound can be prepared from substituted dicyanobenzene.

The phthalocyanine compound according to the present invention can be used for preparation of near-infrared absorption filter, as the pigment of near-infrared absorption filter, according to a conventional method. As a polymer resin for near-infrared absorption filter, most transparent polymer resins such as polymethyl methacrylate, polyester, polycarbonate, polyurethane and so on can be used. But according to each application, material suitable for required conditions such as heat resistance, weather resistance and so on is used. The near-infrared absorption filter can be prepared by coating the solution made by dissolving the near-infrared absorption pigment in solvent, on the polymer resin. As the solvent, various solvent such as methylethylketone, tetrahydrofuran, chloroform, toluene, and so on, can be used.

Hereinafter, the preferable examples are provided for better understanding of the present invention. However, the present invention is not limited by the following examples.

Example 1

Preparation of Vanadium Phthalocyanine 10 g of vanadium oxide phthalocyanine (VOPc) precursor compound $VOPc(2,5-Cl_2PhO)_8\{2,6-(CH_3)_2PhO\}_4F_4$ (wherein, Ph=phenyl) whose UV/VIS maximum absorption wavelength is 752 nm and absorption coefficient($\epsilon$) is 91,200 ml/g·cm, was added into a 3 neck flask having reflux condenser, and reacted with 200 ml of piperidine at 60□ for 2 hours. After completion of the reaction, reaction solution was vacuum-evaporated to obtain vanadium phthalocyanine compound $VOPc(2,5-Cl_2PhO)_8\{2,6-(CH_3)_2PhO\}_4(C_5H_{10}N)_4$. Wherein, at least one of —$C_5H_{10}N$ was positioned at $A_1$, $A_4$, $A_5$, $A_8$, $A_9$, $A_{12}$, $A_{13}$ and $A_{16}$ of Formula 1. The maximum absorption wavelength of the vanadium phthalocyanine compound was 914 nm, and the absorption coefficient of the vanadium phthalocyanine compound was 54,200 ml/g·cm.

Example 2

Preparation of Vanadium Phthalocyanine

Except for using 200 ml of pyrrolidine instead of using 200 ml of piperidine, vanadium phthalocyanine compound VOPc $(2,5-Cl_2PhO)_8\{2,6-(CH_3)_2PhO\}_4(C_4H_8N)_4$ was obtained according to the same manner of Example 1. The maximum absorption wavelength of the vanadium phthalocyanine compound was 910 nm and the absorption coefficient of the vanadium phthalocyanine compound was 54,800 ml/g·cm.

Comparative Example 1

Preparation of Vanadium Phthalocyanine

In a 3 neck flask with reflux condenser, 10 g of 3,4,5,6-tetrafluorophthalonitrile, 10 g of thiophenol, and 7 g of potassium fluoride were added, and 30 ml of acetonitrile as a solvent was added, and stirred at room temperature for 12 hours. After completion of the reaction, 7 g of 2,6-dimethylphenol and 4 g of potassium fluoride were added in the reaction solution, and reflux reacted for 8 hours, and after completion of the reaction, vacuum-evaporated. 20 g of the obtained crude reactant was added into a 3 neck flask with reflux condenser, and reflux reacted with 2 g of vanadium trichloride, 2 g of 1-octanol, and 30 g of benzonitrile for 8 hours. After completion of the reaction, reaction solution was vacuum-evaporated to obtain vanadium phthalocyanine compound precursor $VOPc(PhS)_8\{2,6-(CH_3)_2PhO\}_4F_4$. 10 g of the crude vanadium phthalocyanine compound precursor and 50 ml of cyclohexylamine were added into a 3 neck flask with reflux condenser, and reacted at 60☐ for 8 hours. After completion of the reaction, reaction solution was vacuum-evaporated to obtain vanadium phthalocyanine compound $VOPc(PhS)_8\{2,6-(CH_3)_2PhO\}_4(C_6H_{11}NH)_4$. The maximum absorption wavelength of the vanadium phthalocyanine compound was 933 nm, and the absorption coefficient of the vanadium phthalocyanine compound was 64,200 ml/g·cm.

Experimental Example

Analysis of UV/VIS Spectrum

Figure 2:
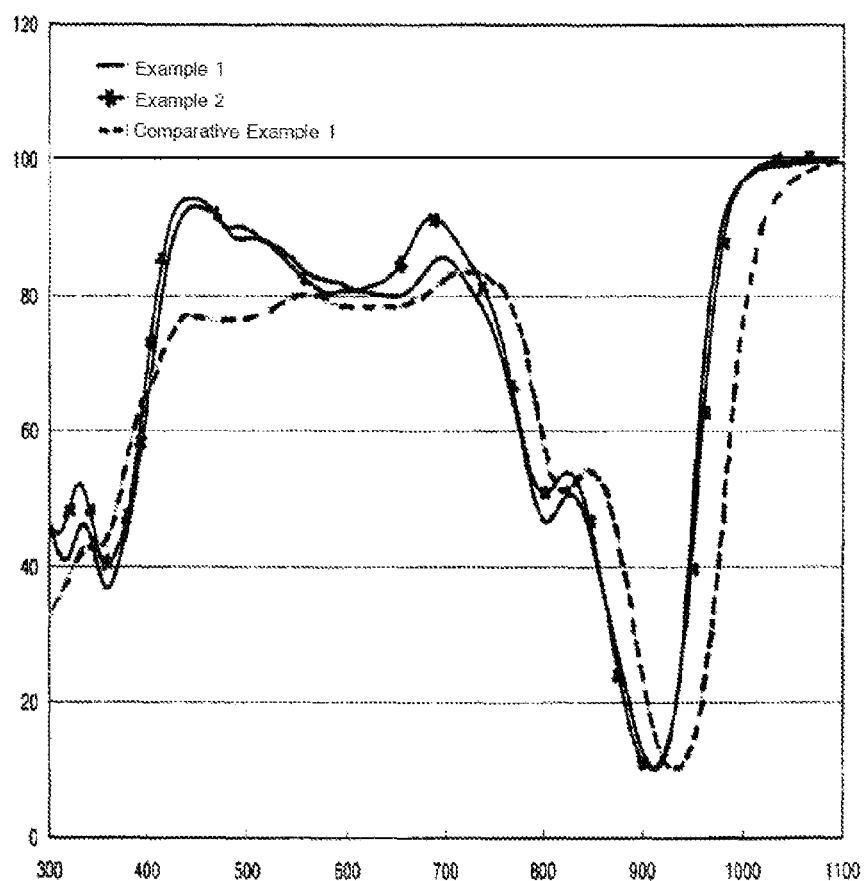
FIG. 2 shows UV/VIS transmission spectra of vanadium phthalocyanine compounds prepared in Example 1 and 2 and Comparative Example 1.

The vanadium phthalocyanine compounds prepared by Example 1 and 2 and Comparative Example 1 were diluted with toluene by 10 ppm, and their UV/VIS spectra were measured. UV/VIS absorption spectra of the vanadium phthalocyanine compounds prepared by Example 1 and 2 and Comparative Example 1 are shown in FIG. 1, from which maximum absorption wavelength and absorption coefficient (ml/g·cm) were calculated. Also, UV/VIS transmission spectra of the vanadium phthalocyanine compounds prepared by Example 1 and 2 and Comparative Example 1 are shown in FIG. 2, which maximum absorption wavelength in the near-infrared light region and transmittance in the visible light region, namely 450 nm were calculated from and shown in the following Table 1. Wherein, the transmittance in the visible light region means the transmittance in the case that transmittance at the maximum absorption wavelength is fixed to 10%.

TABLE 1

|  | Transmittance (450 nm) | Transmittance (maximum absorption wavelength) |
|---|---|---|
| Example 1 | 93.2% | 10% (914 nm) |
| Example 2 | 94.2% | 10% (910 nm) |
| Comparative Example 1 | 77.0% | 10% (933 nm) |

As shown in Table 1, the vanadium phthalocyanine compounds of Example 1 and 2 have superior transmittance in the visible light region, compared with the vanadium phthalocyanine compound of Comparative Example 1.

The invention claimed is:

1. A near-infrared absorption vanadium phthalocyanine compound represented by the following Formula:

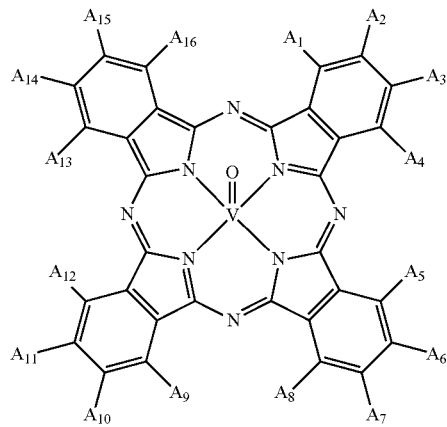

wherein, $A_2$, $A_3$, $A_6$, $A_7$, $A_{10}$, $A_{11}$, $A_{14}$ and $A_{15}$ are independently $OR_1$, $SR_2$ or a halogen atom, wherein at least four thereof are $OR_1$; $A_1$, $A_4$, $A_5$, $A_8$, $A_9$, $A_{12}$, $A_{13}$ and $A_{16}$ are independently $OR_1$, $SR_2$, $NR_3R_4$ or a halogen atom, wherein at least one thereof is $NR_3R_4$, and at least four thereof are $OR_1$; $R_1$, $R_2$, $R_3$ and $R_4$ are independently an alkyl group of 1 to 10 carbon atoms, an aryl group of 6 to 10 carbon atoms, or an aralkyl group of 7 to 15 carbon atoms.

2. The near-infrared absorption vanadium phthalocyanine compound of claim 1, wherein, $R_3$ and $R_4$ are connected to foim a cyclic structure.

3. The near-infrared absorption vanadium phthalocyanine compound of claim 1, wherein, $NR_3R_4$ forms a heterocyclic compound whose structure is selected from the group consisting of pyrrolidine and piperidine.

4. A near-infrared absorption filter comprising the near-infrared absorption vanadium phthalocyanine compound of claim 1.

* * * * *